United States Patent [19]

Schumann

[11] Patent Number: Plant 5,373

[45] Date of Patent: Dec. 18, 1984

[54] GERANIUM PLANT NAMED BLUES

[75] Inventor: Ingeborg Schumann, Bad Ems, Fed. Rep. of Germany

[73] Assignee: Pelargonien-Fischer KG, Hillscheid, Fed. Rep. of Germany

[21] Appl. No.: 548,221

[22] Filed: Nov. 2, 1983

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Koch

[57] ABSTRACT

A new and distinct cultivar of geranium plant named Blues characterized by the combined features of fuchsia pink flower color, semi-double to single flower form, cultivation below 12° C., short peduncles, large flowerhead, compact habit, and excellent branching.

3 Drawing Figures

The present invention comprises a new and distnct cultivar of geranium, botanically known as *Pelargonium zonale,* and hereinafter referred to by the cultivar name Blues.

Blues is a product of planned breeding program which had the objective of creating new geranium cultivars with pink flower color, semi-double flower form, compact habit, fast rooting, good tolerance to botrytis, and superior weather resistance.

Blues was originated from a hybridization made in a controlled breeding program in Hillscheid, Federal Republic of Germany in 1979. The female parent was the unpatented cultivar Highfields Festival, a cultivar having pink semi-double flowers, inferior branching, and slow rooting. The male parent of Blues was a patented cultivar created by self-breeding of an unnamed cultivar designated by number 94, with the male parent having pink flower color with a white eye, single flower form, and compact habit.

Blues was discovered and selected as one flowering plant within the progeny of the stated cross by Ingeborg Schumann on June 27, 1980 in a controlled environment in Hillscheid, Federal Republic of Germany.

The first act of asexual reproduction of Blues was accomplished when vegetative cuttings were taken from the initial selection in January, 1981 in a controlled environment in Hillscheid, Federal Republic of Germany by a technician working under formulations established and supervised by Ingeborg Schumann. Horticultural examination of selected units initiated in the Spring of 1981 and continued in 1982 has demonstrated that the combination of characteristics as herein disclosed for Blues are firmly fixed and are retained through successive generations of asexual reproduction.

Blues has not been observed under all possible environmental conditions. The phenotype may vary significantly with variations in environment such as temperature, light intensity, and day length. The following observations, measurements, and comparisons describe plants grown in Hillscheid, Federal Republic of Germany under greenhouse conditions which approximate those generally used in commercial practice.

The following traits have been repeatedly observed and are determined to be basic characteristics of Blues which in combination distinguish this geranium as a new and distinct cultivar:

1. Fuchsia pink flower color.
2. Semi-double to single flower form.

3. Blues can be cultivated at temperatures below 12° C.
4. No growth treatment necessary for quality.
5. Short peduncles.
6. Large flowerhead (umbel).
7. Compact habit.
8. Excellent branching, producing an average of 4.3 branches per plant.
9. Dark green foliage.

Of the many commercial cultivars known to the present inventor, the most similar in comparison to Blues is Pelfi® Flirt and Pelfi® Rosenquarz. Reference is made to attached Chart A which compares certain characteristics of Blues to those same characteristics of Pelfi® Flirt and Pelfi® Rosenquarz. In general comparison to Pelfi® Flirt, Blues has a shorter internode length and shorter plant height, smaller leaves, better branching, and faster rooting. In comparison to Pelfi® Rosenquarz, Blues has better foliage durability under outdoor and indoor conditions, faster rooting, and good tolerance to botrytis. In addition, the color of Blues is distinctive relative to the color of both of the comparison cultivars.

The accompanying photographic drawings show typical flower and foliage characteristics of Blues, with colors being as true as possible with illustrations of this type. Sheet 1 is a perspective view of a potted plant of Blues. Sheet 2 is a relatively enlarged view of the flowers, buds and foliage, and Sheet 3 is a black and white print of the underside of the leaves of Blues.

In the following description color references are made to The Royal Horticultural Society Color Chart, except where additional color values are given from the Horticultural Color Chart (H.C.C.). The color values were determined between 4:05 and 4:20 P.M. on Aug. 12, 1983 under 20,000 Klux at Hillscheid, Federal Republic of Germany.

CLASSIFICATION

Botanical: A hybrid of the genus *Pelargonium l'hert.*
Commercial: Blues.

INFLORESCENCE

Umbel:

*Average diameter.*—110 mm.
*Average depth.*—88 mm.
*Peduncle length.*—220 mm.

*Pedicel length.*—32 mm.

Corolla:

*Average diameter.*—51 mm.

*Form.*—Nearly single, weak semi-double, round.

*Color (general tonality from a distance of three meters).*—R.H.S. 58C, H.C.C. 625.

*Color (abaxial).*—R.H.S. 55A, H.C.C. 625/1, with white eye at center.

Bud:

*Shape.*—Narrow elliptic.

*Color (abaxial).*—Slightly lighter than corolla.

Reproductive organs:

*Androecium.*—Monodelphous; 7–9 stamens; plentiful pollen.

*Gynoecium.*—4–5 Lobed stigma, deformed.

Spring flowering response period: In Hillscheid, Federal Republic of Germany in 1982, 60% of plants with at least 1 flower opened 13 weeks after planting of unrooted cuttings.

Outdoor flower production: The flower count in 1982 in Hillscheid, Federal Republic of Germany was between 41 and 46 flowers per plant for June through October observation period.

Durability: 100% shatter resistance.

PLANT

Foliage:

*Form.*—Generally kidney shaped.

*Margin.*—Bicrenate.

*Color (abaxial).*—Dark green.

*Tolerance to botrytis.*—Good.

General appearance and form:

*Internode length.*—30 mm.

*Branching pattern.*—An average of 4.3 branches per plant.

*Height.*—235 mm.

CHART A

| | Corolla Color | Branching Habit (number of branches) | Chlorophyll Quality for Transportation | Rooting Time |
|---|---|---|---|---|
| Pelfi ® Flirt | RHS 67C | 3.2 | good | slow |
| Pelfi ® Rosenquarz | RHS 61D | 4.2 | bad | medium |
| Blues | RHS 58C | 4.3 | very good | very fast |

| | Plant Height | Spring Flowering Response | Outdoor Flower Production | Tolerance of Botrytis |
|---|---|---|---|---|
| Pelfi ® Flirt | tall | 55% | 40–44 | medium |
| Pelfi ® Rosenquarz | small | 70% | 52–54 | bad |
| Blues | medium | 60% | 41–46 | good |

I claim:

1. A new and distinct cultivar of geranium plant named Blues, as described and illustrated, and particularly characterized by the combined features of fuchsia pink flower color, semi-double to single flower form, cultivation below 12° C., short peduncles, large flowerhead, compact habit, and excellent branching.

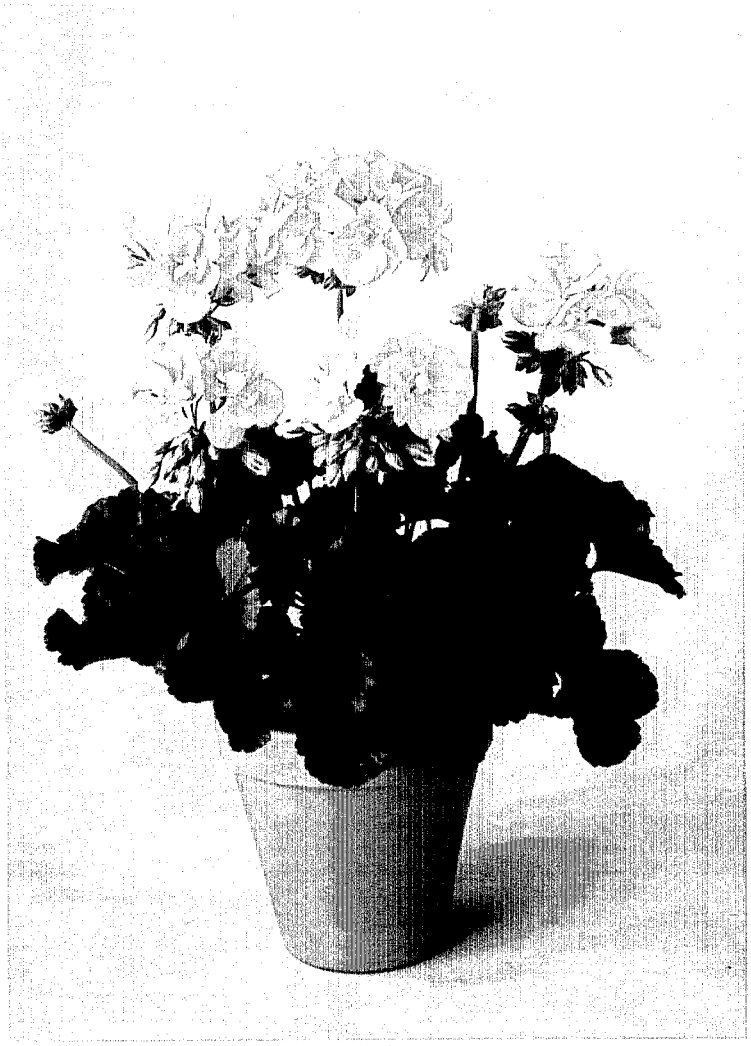

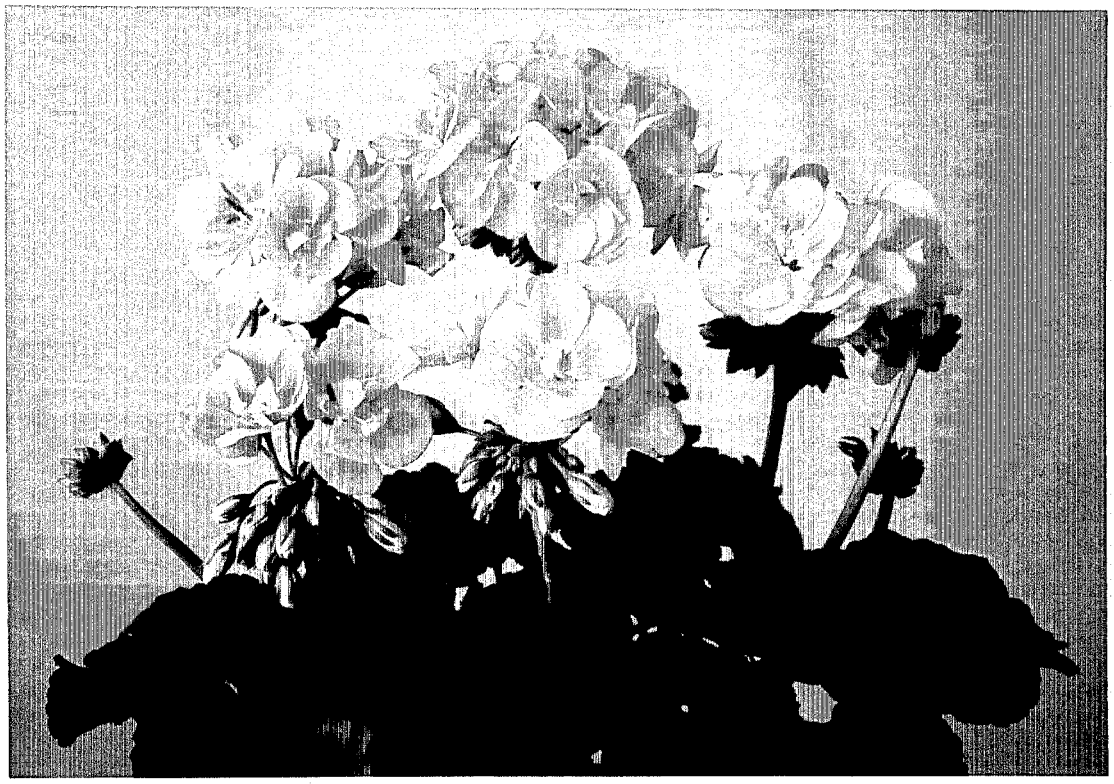

B l u e s
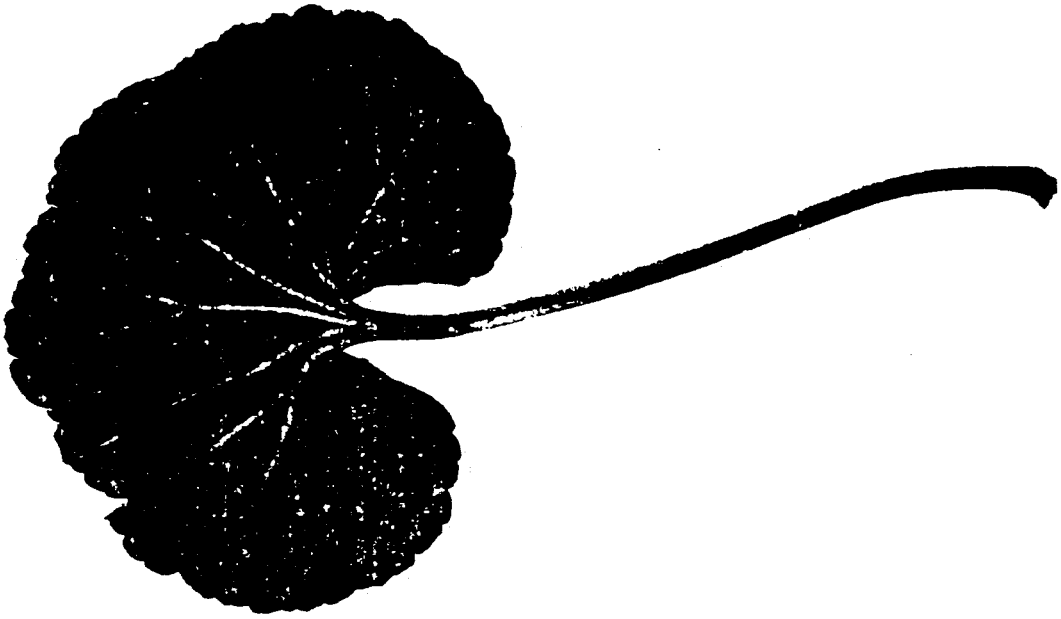
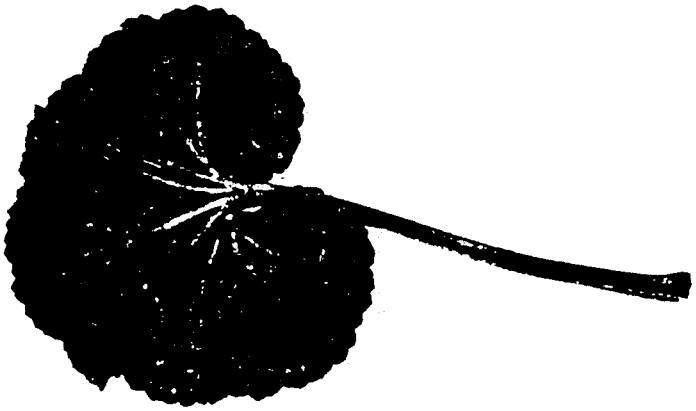

* * * * *